US012569473B2

(12) United States Patent
Dow

(10) Patent No.: US 12,569,473 B2
(45) Date of Patent: Mar. 10, 2026

(54) METHODS TO TREAT RESPIRATORY INFECTION UTILIZING CASTANOSPERMINE ANALOGS

(71) Applicant: 60 Degrees Pharmaceuticals, Inc., Washington, DC (US)

(72) Inventor: Geoffrey S. Dow, Washington, DC (US)

(73) Assignee: 60 Degrees Pharmaceuticals, Inc., Washington, DC (US)

( * ) Notice: Subject to any disclaimer, the term of this patent is extended or adjusted under 35 U.S.C. 154(b) by 428 days.

(21) Appl. No.: 18/218,202

(22) Filed: Jul. 5, 2023

(65) Prior Publication Data

US 2024/0009176 A1 Jan. 11, 2024

Related U.S. Application Data

(60) Provisional application No. 63/358,341, filed on Jul. 5, 2022.

(51) Int. Cl.
*A61K 31/437* (2006.01)
*A61P 31/14* (2006.01)

(52) U.S. Cl.
CPC ............ *A61K 31/437* (2013.01); *A61P 31/14* (2018.01)

(58) Field of Classification Search
CPC .............................. A61K 31/437; A61P 31/14
See application file for complete search history.

(56) References Cited

U.S. PATENT DOCUMENTS

2018/0360809 A1* 12/2018 Vasudevan ........... A61K 9/0019

FOREIGN PATENT DOCUMENTS

WO WO-2014140680 A1 9/2014
WO WO-2014143907 A1 9/2014

OTHER PUBLICATIONS

Kleineher, et. al., Metabolic Modifications by Common Respiratory Viruses and Their Potential as New Antiviral Targets, Viruses 2021, 13, 2068. (Year: 2021).*

Baker et al., *Controlled Release of Biological Active Agents* (1987) (book).

Cavanaugh et al., *A semi-automated neutral red based chemosensitivity assay for drug screening*, 8 Invest. New Drugs 347-354 (1990) (abstract only).

El Najjar et al., *Paramyxovirus Glycoprotein Incorporation, Assembly and Budding Three Way Dance for Infectious Particle Production*, 6 Viruses 3019-3054 (2014).

Goldstein et al., *Respiratory Syncytial Virus Hospitalizations among U.S. Preterm Infants Compared with Term Infants Before and After the 2014 American Academy of Pediatrics Guidance on Immunoprophylaxis*: 2012-2016, 35(14) American Journal of Perinatology 1433-1442 (Dec. 2018).

International Search Report issued in counterpart PCT Application No. PCT/US23/26884 issued on Oct. 30, 2023.

Sidwell et al., *Use of disposable micro-tissue culture plates for antiviral and interferon induction studies*, 22(5) Appl. Microbiol. 797-801 (1971).

Sorbera et al., *Celgosivir*, 30(6) Drugs of the Future 545-552 (2005).

Watanabe et al., *Dose- and schedule-dependent protective efficacy of celgosivir in a lethal mouse model for dengue virus infection informs dosing regimen for a proof of concept clinical trial*, 96(1) Antiviral Research 32-35 (Oct. 2012).

* cited by examiner

*Primary Examiner* — Jeffrey S Lundgren
*Assistant Examiner* — Paul Randall Gauger
(74) *Attorney, Agent, or Firm* — Panitch Schwarze Belisario & Nadel LLP; Erin M. Dunston; Stephany G. Small

(57) ABSTRACT

Methods of treating or preventing a disease resulting from a respiratory syncytial virus (RSV) infection in a human subject is disclosed. The methods disclosed include administering to the human subject a compound of Formula (I), or pharmaceutical composition including a compound of Formula (I). In certain embodiments, the compound is celgosivir.

20 Claims, 2 Drawing Sheets

METHODS TO TREAT RESPIRATORY INFECTION UTILIZING CASTANOSPERMINE ANALOGS

CROSS-REFERENCE TO RELATED APPLICATIONS

This application claims the benefit of U.S. Provisional Application Ser. No. 63/358,341, filed Jul. 5, 2022, which is hereby incorporated by reference herein in its entirety, including any figures, tables, nucleic acid sequences, amino acid sequences, or drawings.

BACKGROUND OF THE INVENTION

Human respiratory syncytial virus (RSV), also known as human orthopneumovirus, is a human pathogen that causes respiratory tract infections. RSV infections are generally mild in healthy adults, often resembling the common cold and generally requiring no treatment or hospitalization. However, RSV infection can be much more problematic in children. RSV is a major cause of lower respiratory tract infections and hospital visits during infancy and childhood. In fact, RSV is likely the most common cause of bronchiolitis and pneumonia in children under one-year of age in the United States. An estimated 60% of infants in the United States are infected with the virus during the first viral season, with nearly 100% of children being infected with RSV during their first 2 years of life. Of those children infected with RSV, 2-3% will require hospitalization for bronchiolitis or pneumonia. Such serious complications from RSV infection are also common in elderly patients. More particularly each year in the United States, more than 50,000 children under the age of 5 and more than 150,000 older adults are hospitalized with RSV infection, with more than 14,000 people dying from RSV infection annually.

As with many other infections, RSV infection induces a protective immune response. However, protective immunity against RSV is known to wane rapidly, thus allowing individuals to be infected multiple times within a relatively short period of time. In fact, it is possible for an infant to become infected with RSV more than once within a several year period, or even within a single RSV season. Young adults can be re-infected every five to seven years.

There is no treatment for RSV that reduces severity of infection or shortens the recovery time. Instead, treatment of RSV infection is limited to supportive care, including administration of supplemental oxygen and fluids, until the virus runs its course. Palivizumab is a monoclonal antibody directed against an RSV surface protein that has been used as a prophylactic drug with moderate success in high risk individuals, e.g., infants that are premature or have either cardiac or lung disease. However, this prophylactic is not exceptionally effective and is expensive, making its use cost-prohibitive in many parts of the world.

Traditional antivirals are often associated with a diminution of activity when the initiation of dosing is delayed relative to viral exposure and/or onset of symptoms. RSV therapeutics that do not target virus directly, but modulate the immune response to infection, have the potential to provide therapeutic benefit more independently of the timing of viral exposure or symptom onset, in either a treatment or prophylactic modality.

Hence, there remains an urgent medical need for the development of an effective method of treating and/or preventing RSV infection.

SUMMARY OF THE INVENTION

The present application pertains to methods of treating or preventing a disease resulting from a respiratory syncytial virus (RSV) infection in a human subject.

In one aspect, the method comprises treating an RSV infection in a human subject by administering to a human subject infected with RSV at least one initial (loading) dose of a compound of Formula (I), (II), and/or (III), or a pharmaceutically acceptable salt thereof, or a pharmaceutical composition comprising a compound of Formula (I), (II), and/or (III), or a pharmaceutically acceptable salt thereof, followed by administration of a plurality of subsequent doses of a compound of Formula (I), (II), and/or (III), or a pharmaceutically acceptable salt thereof, or a pharmaceutical composition comprising a compound of Formula (I), (II), and/or (III), or a pharmaceutically acceptable salt thereof. In certain embodiments, the method further comprises detecting presence of RSV infection prior to or concurrently with administration of the dosages of a compound of Formula (I), (II), and/or (III). In particular embodiments, the human subject is symptomatic for RSV infection at the time of the administration.

In another aspect, the method comprises preventing an RSV infection in a human subject by administering to a human subject at risk of RSV infection at least one initial (loading) dose of a compound of Formula (I), (II), and/or (III), or a pharmaceutically acceptable salt thereof, or a pharmaceutical composition comprising a compound of Formula (I), (II), and/or (III), or a pharmaceutically acceptable salt thereof, followed by administration of a plurality of subsequent doses of a compound of Formula (I), (II), and/or (III), or a pharmaceutically acceptable salt thereof, or a pharmaceutical composition comprising a compound of Formula (I), (II), and/or (III), or a pharmaceutically acceptable salt thereof. In particular embodiments, the human subject is asymptomatic for RSV infection and/or has been diagnosed as RSV negative at the time of the administration. Any suitable method for diagnosis or testing of RSV infection can be used, and such methods are well known in the art, including nucleic acid assays. In other particular embodiments, the human subject is a child that was born preterm. In additional embodiments the preterm child is less than one year of age.

In certain embodiments, a compound of Formula (I), (II), and/or (III) is administered orally, parenterally (e.g., intravenous, intramuscular, intraperitoneal, subcutaneous, etc.) to a patient that is either uninfected, asymptomatically infected, or symptomatically infected. In particular embodiments the parenteral administration is intravenous or intramuscular administration. In certain embodiments, a compound of Formula (I), (II), and/or (III) may be administered parenterally to a patient who is symptomatically infected, for example for a patient who is hospitalized.

When administered parenterally, doses of a compound of Formula (I), (II), and/or (III) may optionally be reduced in comparison to oral dosing, for example by parenterally administering 50%, 25%, 10%, 5%, or 1% of an oral dose. In certain embodiments, a human subject receives a dose of a compound of Formula (I), (II), and/or (III) that is based on the body weight of the subject and is between about 1 mg/kg/day and about 50 mg/kg/day. In particular embodiments, the dosage is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/kg/day. In other embodiments, the dosage is less than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 mg/kg/day. In further embodiments a compound of Formula (I), (II), and/or (III) is administered at a dose of about 1-50 mg/kg/day, about 1.5-40 mg/kg/day, about 2-30 mg/kg/day, about 2.5-20 mg/kg/day, about 3-15 mg/kg/day, about 4-12 mg/kg/day, about 5-10 mg/kg/day, about 6-9 mg/kg/day, or about 7-8 mg/kg/day.

For both methods of treatment and methods of prevention, in certain embodiments the at least one initial (loading) dose comprises about 40 to 600 mg of a compound of Formula (I), (II), and/or (III), or a pharmaceutically acceptable salt thereof. In additional embodiments, each of the plurality of subsequent doses comprises about 25 to about 400 mg of a compound of Formula (I), (II), and/or (III). or a pharmaceutically acceptable salt thereof.

In certain embodiments, the subsequent doses are administered at intervals of from about 6 to about 12 hours. In other embodiments, the subsequent doses are administered about every 6 hours, about every 8 hours, about every 12 hours, or about every 24 hours. In further embodiments, the subsequent doses are administered once, twice, three, four, or five times per day.

In certain embodiments, the total amount of a compound of Formula (I), (II), and/or (III) does not exceed 600 mg per day. In other embodiments the total amount of a single administration of a compound of Formula (I), (II), and/or (III) is 400 mg or less.

In additional embodiments, the subsequent doses are administered for about 1-10 days, about 1-15 days, about 1-20 days, about 1-25 days, about 30 days, about four weeks, about six weeks, about eight weeks, about three months, about four months, about five months, about six months, about seven months, about eight months, about nine months, about ten months, about eleven months, or about one year. In other embodiments, the subsequent doses are administered for about 5-20 days, 5-30 days, 10-40 days, or 10-50 days.

In the various embodiments, the human subject can be an adult or a child. In particular embodiments, the human subject is a child, such as a child of 10 years of age or less, 9 years of age or less, 8 years of age or less, 7 years of age or less, 6 years of age or less, 5 years of age or less, 4 years of age or less, 3 years of age or less, 2 years of age or less, or 1 year of age or less. In other particular embodiments, the human subject is a child of 1 year of age or less that was born preterm. In further particular embodiments, the human subject is an adult of advanced age, such as an adult of 55 years of age or greater, 56 years of age or greater, 57 years of age or greater, 58 years of age or greater, 59 years of age or greater, 60 years of age or great, 61 years of age or greater, 62 years of age or greater, 63 years of age or greater, 64 years of age or greater, 65 years of age or greater, 66 years of age or greater, 67 years of age or greater, 68 years of age or greater, 69 years of age or greater, 70 years of age or greater, 75 years of age or greater, or 80 years of age or greater.

The compound of Formula (I) is represented by the following structure:

(I)

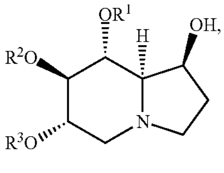

or a pharmaceutically acceptable salt thereof;

wherein $R^1$, $R^2$, and $R^3$ are independently H, $(C_1-C_{14})$ acyl, $(C_1-C_{14})$ alkenylacyl, $(C_3-C_5)$ cycloalkylacyl, $(C_1-C_{14})$ haloalkylacyl $(C_1-C_5)$ alkoxyacyl, or $(C_6-C_{10})$ arylacyl.

In certain embodiments, the compound of Formula (I) is specifically the compound of Formula (II), below, or a pharmaceutically acceptable salt thereof:

(II)

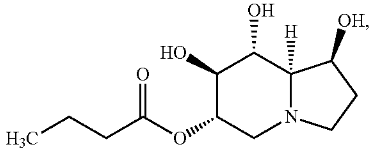

In preferred embodiments, the compound of Formula (I) is a prodrug of castanospermine, a natural product derived from the seeds of *Castanospermum australe*. Once administered compounds of Formula (I) are rapidly converted to castanospermine. Compounds of Formula (I) (e.g., celgosivir) are more rapidly and efficiently absorbed than castanospermine. Compounds of Formula (I) are also more readily absorbed into cells. As a result, compounds of Formula (I) may have higher 50% effective concentration (EC50) values and in vivo efficacy than castanospermine against RSV.

In certain embodiments, the at least one initial dose comprises at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 27, at least 28, at least 29, or at least 30 doses. In other embodiments, the at least one initial dose comprising one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, at most 24, at most 25, at most 27, at most 28, at most 29, or at most 30 doses. In some embodiments, two or more initial doses are administered at intervals of from about 6 to about 12 hours. In other embodiments, two or more initial doses are administered about every 6 hours, about every 8 hours, about every 12 hours, or about every 24 hours. In further embodiments, two or more initial doses are administered once, twice, three, four, or five times per day.

In certain embodiments, the beginning of the administration of the subsequent doses is within a day of administration of the at least one initial dose. In further embodiments, the beginning of the administration of the subsequent doses is about 20 hours, about 15 hours, about 12 hours, about 8 hours, or about 6 hours after administration of the at last one initial dose.

In certain embodiments, at least one initial dose is the same as the subsequent doses, while in other embodiments the at least one initial dose differs from the subsequent doses. In particular embodiments, the at least one initial dose is higher than the subsequent doses. In further embodiments, the at least one initial dose is the same dosage amount throughout the method. In other embodiments, the at least one initial dose varies dosage amounts throughout the method. In further embodiments, the plurality of subsequent doses is the same dosage amount throughout the method. In other embodiments, the plurality of subsequent doses varies dosage amounts throughout the method.

In certain embodiments, for an adult subject, the initial dose can be between about 40 to about 600 mg. In other embodiments, the initial dose in an adult subject can be about 75-600 mg, 100-600 mg, 150-600 mg, about 200-500 mg, or about 250-400 mg. In further embodiments, the initial dose in an adult subject can be about 40 mg, about 60 mg, about 80 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, or about 600 mg. In a further embodiment, the initial dose in an adult subject is between about 550 to about 600 mg. In another embodiment, the initial dose in an adult subject is between about 500 to about 550 mg. In yet another embodiment, the initial dose in an adult subject is between about 450 to about 500 mg. In a further embodiment, the initial dose in an adult subject is between about 400 to about 450 mg. In another embodiment, the initial dose in an adult subject is between about 350 to about 400 mg. In further embodiment, the initial dose in an adult subject is between about 300 to about 350 mg. In yet another embodiment, the initial dose in an adult subject is between about 250 to about 300 mg. In further embodiment, the initial dose in an adult subject is between about 200 to about 250 mg. In another embodiment, the initial dose in an adult subject is between about 150 to about 200 mg. In another embodiment, the initial dose in an adult subject is between about 100 to about 150 mg. In further embodiments, the initial dose in an adult subject is between about 50 to about 100 mg.

The subsequent doses in an adult subject can be between about 40 to about 400 mg. In one embodiment, the subsequent dose in an adult subject is between about 250 to about 300 mg. In another embodiment the subsequent dose in an adult subject is between about 200 to about 250 mg. In yet another embodiment, the subsequent dose in an adult subject is between about 150 to about 200 mg. In a further embodiment, the subsequent dose in an adult subject is between about 100 to about 200 mg. In other embodiments, the subsequent dose in an adult subject is between about 40 to about 80 mg. In even further embodiments, the subsequent dose in an adult subject is between about 80 to about 100 mg. In an additional embodiment, the subsequent dose in an adult subject is between about 125 to about 175 mg. In yet another embodiment, the subsequent dose in an adult subject is about 150 mg.

For a child subject, the initial dose can be between about 15 to about 450 mg. In one embodiment, the initial dose in a child subject is between about 15 to about 25 mg. In another embodiment, the initial dose in a child subject is between about 25 to about 50 mg. In yet another embodiment, the initial dose in a child subject is between about 50 to about 75 mg. In still another embodiment, the initial dose in a child subject is between about 75 to about 100 mg. In further embodiment, the initial dose in a child subject is between about 100 to about 150 mg. In another embodiment, the initial dose in a child subject is between about 150 to about 200 mg. In yet another embodiment, the initial dose in a child subject is between about 200 to about 250 mg. In a further embodiment, the initial dose in a child subject is between about 250 to about 300 mg. In another embodiment, the initial dose in a child subject is between about 300 to about 350 mg. In yet another embodiment, the initial dose in a child subject is between about 350 to about 400 mg. In each instance, the dose can be administered as a single or split dose.

The subsequent doses in a child subject can be between about 15 to about 200 mg. In one embodiment, the subsequent dose in a child subject is between about 15 to about 25 mg. In another embodiment, the subsequent dose in a child subject is between about 25 to about 50 mg. In yet another embodiment, the subsequent dose in a child subject is between about 50 to about 75 mg. In still another embodiment, the subsequent dose in a child subject is between about 75 to about 100 mg. In further embodiment, the subsequent dose in a child subject is between about 100 to about 125 mg. In another embodiment, the subsequent dose in a child subject is between about 125 to about 150 mg. In yet another embodiment, the subsequent dose in a child subject is between about 150 to about 200 mg. In each instance, the dose can eb administered as a single or split dose.

In certain particular embodiments, the child subject is less than one month of age. In particular embodiments, that <1-month old child subject receives an initial dose between about 15 to about 450 mg, or between about 15 to about 250 mg, as a single or split dose. In other embodiments, that <1-month old child receives subsequent doses between about 15 to about 250 mg, or between about 15 to about 250 mg, as single or split doses.

The compounds or pharmaceutical compositions of the present invention can be administered intravenously, orally, rectally or sublingually. In one embodiment, the route of administration is intravenous. In another embodiment, the route of administration is oral. In another embodiment, the route of administration is rectal. In yet another embodiment, the route of administration is sublingual.

The compounds or pharmaceutical compositions of the present invention can be administered as a single or as a divided dose. In some embodiments, the at least one initial dose can be single, divided, or a combination thereof. In some embodiments, the subsequent doses can be single, divided, or a combination thereof. For the subsequent doses in one embodiment, the human subject is administered a divided dose of from about 25 to about 400 mg of a compound of Formula (I), (II), and/or (III), or a pharmaceutical composition comprising a compound of Formula (I), (II), and/or (III), for between about 5 to about 30 days. In another embodiment, the human subject is administered the subsequent doses as a single dose of from about 25 to about 400 mg for between about 5 to about 40 days. In yet another embodiment, the human subject is administered the subsequent doses as a single dose of from about 25 to about 400 mg for between about 5 day to about 60 days. In a further embodiment, the human subject is administered the subsequent doses as a single dose of from about 25 to about 400 mg for between about 5 days to about 60 days. In other versions, the subsequent doses are administered no longer than about 10 days; in yet other versions no longer than about 20 days; in further versions no longer than about 50 days; other versions no longer than about 100 days; and in other versions no longer than about one year.

The invention also relates to methods of preventing a disease resulting from RSV infection by achieving a steady state Cmin serum or plasma concentration of between about 0.05 and about 2.0 microgram/mL of castanospermine in an adult or child subject. In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.3 microgram/mL of castanospermine. In another embodiment, the steady state Cmin serum or plasma concentration achieved in an adult or child subject is between about 0.3 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin serum or plasma concentration achieved in an adult or child subject is between about 1.25 and about 1.75 microgram/mL of castanospermine.

In another aspect of the invention, viral load reduction of human subjects receiving the method of treatment is at least 50% greater than in persons not administered the compound or in placebo-administered groups. In one embodiment, the virological log reduction in human subjects receiving the method of treatment is at least 50% greater than in persons not administered the compound or in placebo-administered groups. In another embodiment, the virological log reduction in human subjects receiving the method of treatment is between about 60% to about 70% greater than in persons not administered the compound or in placebo-administered groups. In another embodiment, the virological log reduction in human subjects receiving the method of treatment is between about 70% to about 80% greater than in persons not administered the compound or in placebo-administered groups. In yet another embodiment, the virological log reduction in human subjects receiving the method of treatment is between about 80 to about 90% greater than in persons not administered the compound or in placebo-administered groups.

BRIEF DESCRIPTION OF THE DRAWINGS

The foregoing will be apparent for the following more particular description of example embodiments of the invention, as illustrated int eh accompanying drawings.

DETAILED DESCRIPTION OF THE INVENTION

Figure 1:
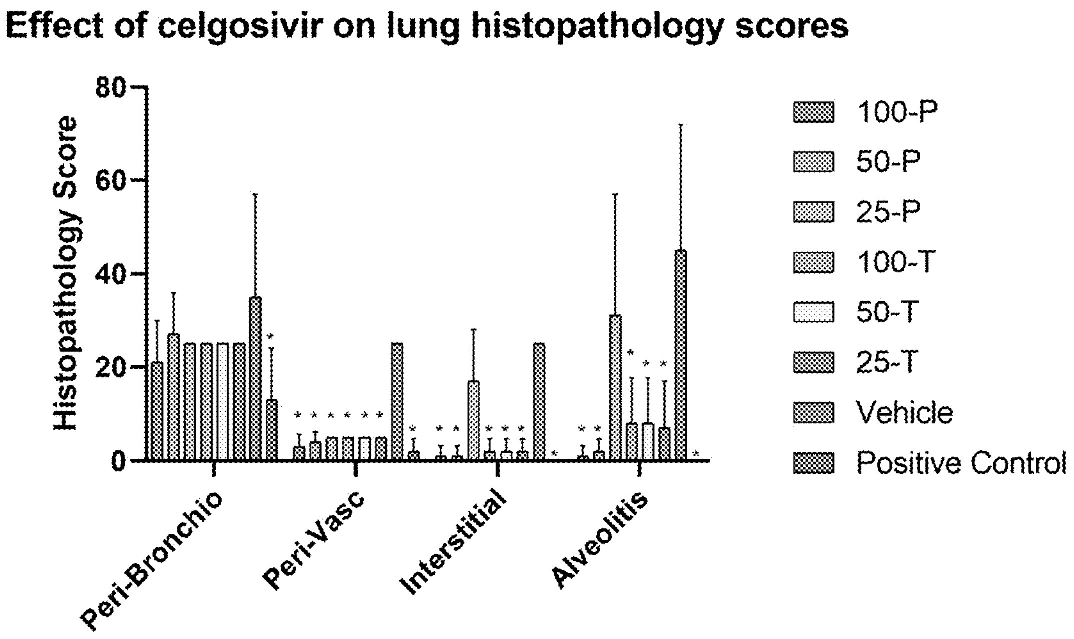
FIG. 1: Effect of celgosivir on lung histopathology scores. Groups of five cotton rats were administered 25, 50 or 100 mg/kg celgosivir twice per day beginning one day prior to infection [prophylaxis, P] or one day after infection [treatment, T], drug vehicle twice per day beginning one day prior to infection [vehicle], or synagis [2.5 mg/kg i.m.] once per day beginning the day after infection [positive control]. On the fifth day post infection, animals were sacrificed and histopathological changes in the lung were scored across four domains [peri-bronchial space, per-vascular space, interstitial space and alveolitis]. The degree of RSV-induced inflammation was reduced for at least one domain for all doses of celgosivir evaluated. The degree of RSV-induced inflammation was reduced for at least one domain for all doses of celgosivir evaluated. Statistical significance from the vehicle control is indicated by an asterix [P<0.05].

A description of example embodiments of the invention follows.

Definitions

All definitions of substituents set forth below are further applicable to the use of the term in conjunction with another substituent. Unless defined otherwise, all technical and scientific terms used herein have the same meaning as commonly understood by one of ordinary skill in the art to which this invention belongs.

"Alkyl" as used alone or as part of a larger moiety as in "arylalkyl" or "aryloxyalkyl" means a saturated aliphatic branched or straight-chain monovalent hydrocarbon radicals, typically $C_1$-$C_{16}$, preferably $C_1$-$C_{12}$. For example, "($C_1$-$C_6$) alkyl" means a radical having from 1-6 carbon atoms in a linear or branched arrangement. "($C_1$-$C_6$) alkyl" includes methyl, ethyl, propyl, butyl, tert-butyl, pentyl and hexyl.

"Alkylene" means a saturated aliphatic straight-chain divalent hydrocarbon radical. Thus, "($C_1$-$C_6$) alkylene" means a divalent saturated aliphatic radical having from 1-6 carbon atoms in a linear arrangement. "($C_1$-$C_6$) alkylene" includes methylene, ethylene, propylene, butylene, pentylene and hexylene.

"Cycloalkyl" means saturated aliphatic cyclic hydrocarbon ring. Thus, "$C_3$-$C_8$ cycloalkyl" means (3-8 membered) saturated aliphatic cyclic hydrocarbon ring. $C_3$-$C_8$ cycloalkyl includes, but is not limited to cyclopropyl, cyclobutyl, cyclopentyl, cyclohexyl, cycloheptyl, and cyclooctyl. Preferably, cycloalkyl is $C_3$-$C_6$ cycloalkyl.

The term "alkoxy" means —O-alkyl; "arylalkoxy" means an alkoxy group substituted at any carbon by an aryl group; "hydroxyalkyl" means alkyl substituted with hydroxy; "arylalkyl" means alkyl substituted with an aryl group; "alkoxyalkyl" mean alkyl substituted with an alkoxy group; "cycloalkylalkyl" means alkyl substituted with cycloalkyl; "alkylcarbonyl" means —C(O)-A*, wherein A* is alkyl; "alkoxycarbonyl" means —C(O)—OA*, wherein A* is alkyl; and where alkyl is as defined above. Alkoxy is preferably O($C_1$-$C_6$) alkyl and includes methoxy, ethoxy, propoxy, butoxy, pentoxy and hexoxy.

"Cycloalkoxy" means a cycloalkyl-O— group wherein the cycloalkyl is as defined above. Exemplary ($C_3$-$C_7$) cycloalkyloxy groups include cyclopropoxy, cyclobutoxy, cyclopentoxy, cyclohexoxy and cycloheptoxy.

"Halogen" and "halo" are interchangeably used herein and each refers to fluorine, chlorine, bromine, or iodine.

The terms "haloalkyl", "halocycloalkyl" and "haloalkoxy" mean alkyl, cycloalkyl, or alkoxy, as the case may be, substituted with one or more halogen atoms. The term "halogen" or "halo" means F, Cl, Br or I.

"Acyl" refers to R"-C(O)—, where R" is H, alkyl, substituted alkyl, heteroalkyl, substituted heteroalkyl, alkenyl, substituted alkenyl, aryl, alkylaryl, or substituted alkylaryl, and is indicated in the general formula of a particular embodiment as "Ac".

An "alkylene group" is represented by $—[CH_2]_z—$, wherein z is a positive integer, preferably from one to eight, more preferably from one to four.

An "alkenylene group" is an alkylene in which at least a pair of adjacent methylenes are replaced with —CH═CH—.

The term "($C_6$-$C_{10}$) aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-10 ring atoms. A "substituted aryl group" is substituted at any one or more substitutable ring atom. The term "$C_6$-$C_{16}$ aryl" as used herein means a monocyclic, bicyclic or tricyclic carbocyclic ring system containing from 6 to 16 carbon atoms and includes phenyl (Ph), naphthyl, anthracenyl, 1,2-dihydronaphthyl, 1,2,3,4-tetrahydronaphthyl, fluorenyl, indanyl, indenyl and the like. The ($C_6$-$C_{10}$) aryl ($C_1$-$C_6$) alkyl group connects to the rest of the molecule through the ($C_1$-$C_6$) alkyl portion of the ($C_6$-$C_{10}$) aryl ($C_1$-$C_6$) alkyl group.

The term "Alkenyl" as used alone or as part of a larger moiety as in "Alkenylacyl" or "haloalkylacyl" means a straight or branched hydrocarbon radical having a specified number of carbon atoms and includes at least one double bond. An alkenyl group generally has between 2 and 6 carbon atoms. The ($C_6$-$C_{10}$) aryl ($C_2$-$C_6$) alkenyl group connects to the remainder of the molecule through the ($C_2$-$C_6$) alkenyl portion of ($C_6$-$C_{10}$) aryl ($C_2$-$C_6$) alkenyl.

"Alkenylacyl" refers to an acyl group, R"-C(O)—, where R" is an alkenyl or a substituted alkenyl (e.g., $CH_3$—CH═CH—C(O)—).

"Pharmaceutically acceptable carrier" means non-therapeutic components that are of sufficient purity and quality for use in the formulation of a composition of the invention that, when appropriately administered to typically do not produce an adverse reaction, and that are used as a vehicle for a drug substance (e.g., a compound of Formula (I)).

"Intraperitoneal injection," as used herein, refers to the injection of a substance into the peritoneum (body cavity).

"Three times a day dosing" or "three times per day," as used herein, refers to three administrations of a composition per every 24-hour period.

"Four times a day dosing" (QDS) or "four times per day," as used herein, refers to four administrations of a composition per every 24-hour period.

As used herein, "BDI" refers to twice daily. Further, as used herein, "QD" refers to once daily.

As used herein, "Cmin" refers to the minimum concentration that a drug achieves after the drug has been administered and prior to the administration of a second or additional dose. Further, "Cmax", as used herein, refers to the maximum concentration. Similarly, "Tmax", as used herein, refers to the time of maximum concentration. Additionally, "AUC", used herein, is the area under the concentration-time curve. Additionally, "50% effective concentration" (EC50), as used herein, refers to the concentration of an anti-viral that produces 50% of the maximal possible antiviral effect.

As used herein, the term "about" refers to a number that differs from the given number by less than 10%. In other embodiments, the term "about" indicates that the number differs from the given number by less than 9%, 8%, 7%, 6%, 5%, 4%, 3%, 2%, or 1%.

As used herein, "viral load" refers to the amount of virus in the blood stream of a human subject.

As used herein, "initial dose" refers to the dose(s) which is administered to an asymptomatic human subject. Further, "loading dose" and "initial dose" have the same meaning and are used interchangeably herein.

As used herein, "asymptomatic" refers to a human subject that may or may not have been exposed to RSV but does not present symptoms related to RSV infection.

As used herein "preventing" or "prevention" refers to achieving, partially, substantially, or completely, one or more of the following results: avoiding the disease, disorder, or syndrome resulting from RSV infection; avoiding clinical symptom or indicator associated with a disease, disorder, or syndrome resulting from RSV infection; reducing the severity of the disease, disorder, or syndrome resulting from RSV infection; or avoiding RSV infection.

Dosing Regimen

The present invention pertains to methods of preventing or treating a disease resulting from RSV infection in a human subject, the method comprising administering to a human subject at least one initial (loading) dose of a compound of Formula (I), (II), and/or (III), or a pharmaceutically acceptable salt thereof, or a pharmaceutical composition comprising a compound of Formula (I), (II), and/or (III), or a pharmaceutically acceptable salt thereof, followed by administration of a plurality of subsequent doses of a compound of Formula (I), (II), and/or (III), or a pharmaceutically acceptable salt thereof, or a pharmaceutical composition comprising a compound of Formula (I), (II), and/or (III), or a pharmaceutically acceptable salt thereof.

In certain embodiments, the method is for prevention of disease from RSV infection. In such embodiments, the human subject may be asymptomatic for RSV infection at the time of the administration and/or has been diagnosed as RSV negative at the time of the administration. Any suitable method for diagnosis or testing of RSV infection can be used, and such methods are well known in the art, including nucleic acid assays. In particular embodiments, the human subject is a child that was born preterm. In additional embodiments the preterm child is less than one year of age.

In other embodiments, the method is for treatment of RSV infection. In such embodiments, the human subject may be symptomatic for RSV infection at the time of the administration and/or the human subject may have been determined to be currently infected with RSV at the time of the administration. In particular embodiments, the method further comprises detecting presence of RSV infection prior to or concurrently with administration of the dosages of a compound of Formula (I), (II), and/or (III).

For both methods of treatment and methods of prevention, in certain embodiments the at least one initial (loading) dose comprises about 40 to 600 mg of a compound of Formula (I), (II), and/or (III), or a pharmaceutically acceptable salt thereof. In additional embodiments, each of the plurality of subsequent doses comprises about 25 to about 400 mg of a compound of Formula (I), (II), and/or (III), or a pharmaceutically acceptable salt thereof.

In certain embodiments, the total amount of a compound of Formula (I), (II), and/or (III) does not exceed 600 mg per day. In other embodiments the total amount of a single administration of a compound of Formula (I), (II), and/or (III) is 400 mg or less.

In further embodiments, the subsequent doses are administered at intervals of from about 6 to about 12 hours. In other embodiments, the subsequent doses are administered about every 6 hours, about every 8 hours, about every 12 hours, or about every 24 hours. In further embodiments, the subsequent doses are administered once, twice, three, four, or five times per day. In additional embodiments, the subsequent doses are administered for about 1-10 days, about 1-15 days, about 1-20 days, about 1-25 days, about 30 days, about four weeks, about six weeks, about eight weeks, about three months, about four months, about five months, about six months, about seven months, about eight months, about nine months, about ten months, about eleven months, or about one year. In other embodiments, the subsequent doses are administered for about 5-20 days, 5-30 days, 10-40 days, or 10-50 days.

In the various embodiments, the human subject can be an adult or a child. As used herein, a "child" refers to a human subject who is between the ages of 1 day to <18 years of age. The term "adult" refers to a human subject who is 18 years of age or older. In particular embodiments, the human subject is a child, such as a child of 10 years of age or less, 9 years of age or less, 8 years of age or less, 7 years of age or less, 6 years of age or less, 5 years of age or less, 4 years of age or less, 3 years of age or less, 2 years of age or less, or 1 year of age or less. In other particular embodiments, the human subject is a child of 1 year of age or less that was born preterm. In further particular embodiments, the human subject is an adult of advanced age, such as an adult of 55 years of age or greater, 56 years of age or greater, 57 years of age or greater, 58 years of age or greater, 59 years of age or greater, 60 years of age or great, 61 years of age or greater, 62 years of age or greater, 63 years of age or greater, 64 years of age or greater, 65 years of age or greater, 66 years of age or greater, 67 years of age or greater, 68 years of age or greater, 69 years of age or greater, 70 years of age or greater, 75 years of age or greater, or 80 years of age or greater. Further, the plurality of human subjects may include adults or children. In some embodiments, the plurality of human subjects may include only adults. In another embodiment, the plurality of human subjects may include only children. In yet another embodiment, the plurality of human subjects may include both adults and children.

In one embodiment, the compound of the invention is a compound of Formula (I):

(I)

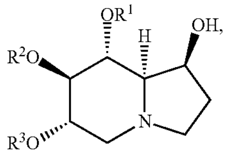

or a pharmaceutically acceptable salt there of;

wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

In another embodiment, $R^1$ and $R^2$ are H and $R^3$ is a ($C_1$-$C_{14}$) acyl. In another embodiment, $R^1$ is $CH_3$—$CH_2CH_2$—C(O)—. In yet another embodiment, $R^2$ is $CH_3$—$CH_2CH_2$—C(O)—. In a further embodiment, $R^3$ is $CH_3$—$CH_2CH_2$—C(O)—. In another embodiment, at least one but not more than two $R^1$, $R^2$, and $R^3$ is a hydrogen.

In yet another embodiment, the compound of the invention is a compound of Formula (II):

(II)

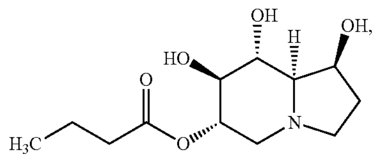

or a pharmaceutically acceptable salt thereof.

The compound of Formula (II), or pharmaceutical composition comprising a compound of Formula (II), can be used in any of the embodiments provided herein for Formula (I).

In further embodiment, the compound of the invention is a compound of Formula (III):

(III)

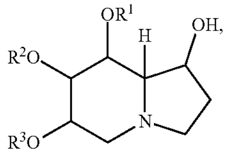

or a pharmaceutically acceptable salt there of, wherein $R^1$, $R^2$, and $R^3$ are independently H, ($C_1$-$C_{14}$) acyl, ($C_1$-$C_{14}$) alkenylacyl, ($C_3$-$C_8$) cycloalkylacyl, ($C_1$-$C_{14}$) haloalkylacyl ($C_1$-$C_8$) alkoxyacyl, or ($C_6$-$C_{10}$) arylacyl.

The compound of Formula (III), or pharmaceutical composition comprising a compound of Formula (III), can be used in any of the embodiments provided herein for Formula (I).

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention.

The compounds of the present invention can be administered as the free base or as a pharmaceutically acceptable salt. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estotate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. In one embodiment, the compound of Formula (I) is a hydrochloride salt. In another embodiment, the compound of Formula (II) is a hydrochloride salt.

The invention is also directed to methods of the invention using a pharmaceutical composition comprising a compound of Formula (I), (II), or (III). The disclosed compounds of Formula (I) and Formula (II) can be administered to the subject in conjunction with an acceptable pharmaceutical carrier or diluent as part of a pharmaceutical composition for prevention or treatment of a disease resulting from RSV infection, and according to any of the dosing regimens described herein. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, PA. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

In one embodiment, the pharmaceutical composition comprises a pharmaceutically acceptable carrier or diluent and a compound Formula (I), (II), and/or (III).

In preferred embodiments, the compound is prodrug of castanospermine, a natural product derived from the seeds of *Castanospermum australe*. In another embodiment, the compound of Formula (I), (II), or (III) is converted to castanospermine after administration to a human subject. In yet another embodiment, a steady state Cmin serum or plasma concentration of between about 0.05 and about 2.0 microgram/mL of castanospermine in an adult or child human subject is attained. Compounds of Formula (I), (II), or (III) (e.g., celgosivir) are more rapidly and efficiently absorbed into cells than castanospermine. As a result, the claimed compounds may have higher EC50 values and in vivo efficacy than castanospermine against RSV.

The human subject can be administered a compound of the present invention for a period of about between about 1 day to about one year. In one embodiment, the subsequent doses are administered for about 5 to about 180 days. In further embodiment, the subsequent doses are administered for about 30 to about 120 days. In another embodiment, the subsequent doses are administered for about 60 to about 90 days. In yet another embodiment, the subsequent doses are administered for about 90 to about 120 days. In another embodiment, the subsequent doses are administered for about 120 days to about six months.

In certain embodiments, the at least one initial dose comprises at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 27, at least 28, at least 29, or at least 30 doses. In other embodiments, the at least one initial dose comprising one, at most two, at most three, at most four, at most five, at most six, at most seven, at most eight, at most nine, at most ten, at most 11, at most 12, at most 13, at most 14, at most 15, at most 16, at most 17, at most 18, at most 19, at most 20, at most 21, at most 22, at most 23, at most 24, at most 25, at most 27, at most 28, at most 29, or at most 30 doses. In some embodiments, two or more initial doses are administered at intervals of from about 6 to about 12 hours. In other embodiments, two or more initial doses are administered about every 6 hours, about every 8 hours, about every 12 hours, or about every 24 hours. In further embodiments, two or more initial doses are administered once, twice, three, four, or five times per day.

In certain embodiments, the beginning of the administration of the subsequent doses is within a day of administration of the at least one initial dose. In further embodiments, the beginning of the administration of the subsequent doses is about 20 hours, about 15 hours, about 12 hours, about 8 hours, or about 6 hours after administration of the at last one initial dose.

In certain embodiments, at least one initial dose is the same as the subsequent doses, while in other embodiments the at least one initial dose differs from the subsequent doses. In particular embodiments, the at least one initial dose is higher than the subsequent doses. In further embodiments, the at least one initial dose is the same dosage amount throughout the method. In other embodiments, the at least one initial dose varies dosage amounts throughout the method. In further embodiments, the plurality of subsequent doses is the same dosage amount throughout the method. In other embodiments, the plurality of subsequent doses varies dosage amounts throughout the method.

In certain embodiments, for an adult subject, the initial dose can be between about 40 to about 600 mg. In other embodiments, the initial dose in an adult subject can be about 75-600 mg, 100-600 mg, 150-600 mg, about 200-500 mg, or about 250-400 mg. In further embodiments, the initial dose in an adult subject can be about 40 mg, about 60 mg, about 80 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, or about 600 mg. In a further embodiment, the initial dose in an adult subject is between about 550 to about 600 mg. In another embodiment, the initial dose in an adult subject is between about 500 to about 550 mg. In yet another embodiment, the initial dose in an adult subject is between about 450 to about 500 mg. In a further embodiment, the initial dose in an adult subject is between about 400 to about 450 mg. In another embodiment, the initial dose in an adult subject is between about 350 to about 400 mg. In further embodiment, the initial dose in an adult subject is between about 300 to about 350 mg. In yet another embodiment, the initial dose in an adult subject is between about 250 to about 300 mg. In further embodiment, the initial dose in an adult subject is between about 200 to about 250 mg. In another embodiment, the initial dose in an adult subject is between about 150 to about 200 mg. In another embodiment, the initial dose in an adult subject is between about 100 to about 150 mg. In further embodiments, the initial dose) in an adult subject is between about 50 to about 100 mg.

The subsequent doses in an adult subject can be between about 40 to about 400 mg. In one embodiment, the subsequent dose in an adult subject is between about 250 to about 300 mg. In another embodiment the subsequent dose in an adult subject is between about 200 to about 250 mg. In yet another embodiment, the subsequent dose in an adult subject is between about 150 to about 200 mg. In a further embodiment, the subsequent dose in an adult subject is between about 100 to about 200 mg. In other embodiments, the subsequent dose in an adult subject is between about 40 to about 80 mg. In even further embodiments, the subsequent dose in an adult subject is between about 80 to about 100 mg. In an additional embodiment, the subsequent dose in an adult subject is between about 125 to about 175 mg. In yet another embodiment, the subsequent dose in an adult subject is about 150 mg.

For a child subject, the initial dose in a child subject can be between about 15 to about 450 mg. In one embodiment, the initial dose in a child subject is between about 15 to about 25 mg. In another embodiment, the initial dose in a child subject is between about 25 to about 50 mg. In yet another embodiment, the initial dose in a child subject is between about 50 to about 75 mg. In still another embodiment, the initial dose in a child subject is between about 75 to about 100 mg. In further embodiment, the initial dose in a child subject is between about 100 to about 150 mg. In another embodiment, the initial dose in a child subject is between about 150 to about 200 mg. In yet another embodiment, the initial dose in a child subject is between about 200 to about 250 mg. In a further embodiment, the initial dose in a child subject is between about 250 to about 300 mg. In another embodiment, the initial dose in a child subject is between about 300 to about 350 mg. In yet another embodiment, the initial dose in a child subject is between about 350 to about 400 mg. In each instance, the dose can be administered as a single or split dose.

The subsequent doses in a child subject can be between about 25 to about 200 mg. In one embodiment, the subsequent dose in a child subject is between about 25 to about 50 mg. In another embodiment, the subsequent dose in a child subject is between about 50 to about 75 mg. In yet another embodiment, the subsequent dose in a child subject is between about 75 to about 100 mg. In further embodiment, the subsequent dose in a child subject is between about 100 to about 125 mg. In another embodiment, the subsequent dose in a child subject is between about 125 to about 150 mg. In yet another embodiment, the subsequent dose in a child subject is between about 150 to about 200 mg.

In certain particular embodiments, the child subject is less than one month of age. In particular embodiments, that <1-month old child subject receives an initial dose between about 15 to about 450 mg, or between about 15 to about 250 mg, as a single or split dose. In other embodiments, that <1-month old child receives subsequent doses between about 15 to about 250 mg, or between about 15 to about 250 mg, as single or split doses.

In certain embodiments of the invention, the initial dose (s) and/or the subsequent doses are administered three times per day, wherein each dose is about 167 mg to about 200 mg. In other embodiments, initial dose(s) and/or the subsequent doses are administered four times per day, wherein each dose is about 125 mg to about 150 mg. In one embodiment, the initial dose(s) and/or the subsequent doses are administered as two divided doses, wherein the total daily dose is about 225 mg to about 600 mg. In another embodiment, the initial dose(s) and/or the subsequent doses are administered as two divided doses, wherein the total daily dose is about 75 mg to about 600 mg. In other embodiments, the initial dose(s) and/or the subsequent doses are administered as two divided doses, wherein each dose is about 250 mg to about 300 mg. In yet another embodiment, the initial dose(s) and/or the subsequent doses are administered as one dose per day, wherein the total daily dose is about 40 mg to about 400 mg. In further embodiments, the initial dose(s) and/or the subsequent doses are administered as one dose per day, wherein each dose is about 225 mg to about 400 mg.

In another embodiment, the initial dose(s) and and/or subsequent doses are about 225 mg, about 240 mg, about 260 mg, about 280 mg, about 320 mg, about 340 mg, about 360 mg, about 380 mg, or about 400 mg and are administered to the human subject once a day. In other embodiments, the initial dose(s) and/or the subsequent doses are about 110 mg, about 225 mg, about 260 mg, about 280 mg, or about 300 mg and administered to the human subject twice a day. In further embodiments, the initial dose(s) and/or the subsequent doses are about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg and are administered to the human subject three times per day. In yet other embodiments, the initial dose(s) and/or the subsequent doses are about 40 mg, about 50 mg, about 60 mg, about 70 mg, about 80 mg, about 90 mg, about 100 mg, about 110 mg, about 120 mg, about 130 mg, about 140 mg, about 150 mg and are administered to the human subject four times per day.

In one embodiment of the invention, the human subject is administered the initial dose(s) and/or the subsequent doses once per day, wherein each dose is about 3.8 mg/kg to about 6.7 mg/kg. In other embodiments, the human subject is administered the initial dose(s) and/or the subsequent doses twice per day, wherein each dose is about 4.2 mg/kg to about 5 mg/kg. In further embodiments, the human subject is administered the initial dose(s) and/or the subsequent doses three times per day, wherein each dose is about 2.8 mg/kg to about 3.33 mg/kg. In yet other embodiments, the human subject is administered the initial dose(s) and/or the subsequent doses four times per day, wherein each dose is about 2.1 mg/kg to about 2.5 mg/kg.

In one embodiment of the invention, the human subject is administered an initial dose of about 150 mg is administered a subsequent dose of about 100 mg every 6 hours for about 5 to about 30 days. In another embodiment, the human subject is administered an initial dose of about 150 mg and is administered a subsequent dose of about 100 mg every 6 hours for about 30 to about 90 days. In yet another embodiment, the human subject is administered an initial dose of about 150 mg and is administered a subsequent dose of about 100 mg every 6 hours for about 90 days to about six months. In further embodiment, the human subject is administered an initial dose of about 150 mg and is administered a subsequent dose of about 100 mg every 8 hours for about 5 to about 30 days. In certain embodiment, the human subject is administered an initial dose of about 150 mg and is administered a subsequent dose of about 100 mg every 8 hours for about 30 to about 90 days. In another embodiment, the human subject is administered an initial dose of about 150 mg and is administered a subsequent dose of about 100 mg every 8 hours for about 90 days to about six months. In yet another embodiment, the human subject is administered an initial dose of about 150 mg and is administered a subsequent dose of about 100 mg every 12 hours for about 5 to about 30 days. In another embodiment, the human subject is administered an initial dose of about 150 mg and is administered a subsequent dose of about 100 mg every 12 hours for about 30 to about 90 days. In further embodiment, the human subject is administered an initial dose of about 150 mg and is administered a subsequent dose of about 100 mg every 12 hours for about 90 days to about six months. In yet another embodiment, the human subject is administered an initial dose of about 150 mg and is administered a subsequent dose of about 150 mg every 6 hours for about 5 to about 30 days. In another embodiment, the human subject is administered an initial dose of about 150 mg and is administered a subsequent dose of about 150 mg every 6 hours for about 30 to about 90 days. In yet another embodiment, the human subject is administered an initial dose of about 150 mg and is administered a subsequent dose of about 150 mg every 6 hours for about 90 days to about six months. In another embodiment, the human subject is administered an initial dose of about 150 mg and is administered a subsequent dose of about 150 mg every 8 hours for about 5 to about 30 days. In certain embodiment, the human subject is administered an initial dose of about 150 mg and is administered a subsequent dose of about 150 mg every 8 hours for about 30 to about 90 days. In yet another embodiment, the human subject is administered an initial dose of about 150 mg and is administered a subsequent dose of about 150 mg every 8 hours for about 90 days to about six months. In one embodiment, the human subject is administered an initial dose of about 150 mg and is administered a subsequent dose of about 150 mg every 12 hours for about 5 to about 30 days. In further embodiment, the human subject is administered an initial dose of about 150 mg and is administered a subsequent dose of about 150 mg every 12 hours for about 30 to about 90 days. In yet another embodiment, the human subject is administered an initial dose of about 150 mg and is administered a subsequent dose of about 150 mg every 12 hours for about 90 days to about six months. In another embodiment, the human subject is administered an initial dose of about 150 mg and is administered a subsequent dose of about 200 mg every 6 hours for about 5 to about 30 days. In one embodiment, the human subject is administered an initial dose of about 150 mg and is administered a subsequent dose of about 200 mg every 6 hours for about 30 to about 90 days. In another embodiment, the human subject is administered an initial dose of about 150 mg and is administered a subsequent dose of about 200 mg every 6 hours for about 90 days to about six months. In further embodiment, wherein the human subject is administered an initial dose of about 150 mg and is administered a subsequent dose of about 200 mg every 8 hours for about 5 to about 30 days. In yet another embodiment, the human subject is administered an initial dose of about 150 mg and is administered a subsequent dose of about 200 mg every 8 hours for about 30 to about 90 days. In one embodiment, the human subject is administered an initial dose of about 150 mg and is administered a subsequent dose of about 200 mg every 8 hours for about 90 days to about six months. In another embodiment, the human subject is administered an initial dose of about 150 mg and is administered a subsequent dose of about 200 mg every 12 hours for about 5 to about 30 days. In further embodiment, the human subject is administered an initial dose of about 150 mg and is administered a subsequent dose of about 200 mg every 12 hours for about 30 to about 90 days. In another embodiment, the human subject is administered an initial dose of about 150 mg and is administered a subsequent dose of about 200 mg every 12 hours for about 90 days to about six months. In certain embodiment, the human subject is administered an initial dose of about 200 mg and is administered a subsequent dose of about 100 mg every 6 hours for about 5 to about 30 days. In yet another embodiment, the human subject is administered an initial dose of about 200 mg and is administered a subsequent dose of about 100 mg every 6 hours for about 30 to about 90 days. In another embodiment, the human subject is administered an initial dose of about 200 mg and is administered a subsequent dose of about 100 mg every 6 hours for about 90 days to about six months. In one embodiment, the human subject is administered an initial dose of about 200 mg and is administered a subsequent dose of about 100 mg every 8 hours for about 5 to about 30 days. In further embodiment, the human subject is administered an initial dose of about 200 mg and is administered a subsequent dose of about 100 mg every 8 hours for about 30 to about 90 days. In yet another embodiment, the human subject is administered an initial dose of about 200 mg and is administered a subsequent dose of about 100 mg every 8 hours for about 90 days to about six months. In another embodiment, the human subject is administered an initial dose of about 200 mg and is administered a subsequent dose of about 100 mg every 12 hours for about 5 to about 30 days. In one embodiment, the human subject is administered an initial dose of about 200 mg and is administered a subsequent dose of about 100 mg every 12 hours for about 30 to about 90 days. In another embodiment, the human subject is administered an initial dose of about 200 mg and is administered a subsequent dose of about 100 mg every 12 hours for about 90 days to about six months. In further embodiment, the human subject is administered an initial dose of about 200 mg and is administered a subsequent dose of about 150 mg every 6 hours for about 5 to about 30 days. In another embodiment of the invention, the human subject is administered an initial dose of about 200 mg and is administered a subsequent dose of about 150 mg every 6 hours for about 30 to about 90 days. In yet another embodiment, the human subject is administered an initial dose of about 200 mg and is administered a subsequent dose of about 150 mg every 6 hours for about 90 days to about six months. In another embodiment, the human subject is administered an initial dose of about 200 mg and is administered a subsequent dose of about 150 mg every 8 hours for about 5 to about 30 days. In one embodiment, the human subject is administered an initial dose of about 200 mg and is administered a subsequent dose of about 150 mg every 8 hours for about 30 to about 90 days. In yet another embodiment, the human subject is administered an initial dose of about 200 mg and is administered a subsequent dose of about 150 mg every 8 hours for about 90 days to about six months. In another embodiment, the human subject is administered an initial dose of about 200 mg and is administered a subsequent dose of about 150 mg every 12 hours for about 5 to about 30 days. In another embodiment, the human subject is administered an initial dose of about 200 mg is administered a subsequent dose of about 150 mg every 12 hours for about 30 to about 90 days. In an embodiment of the invention, the human subject is administered an initial dose of about 200 mg and is administered a subsequent dose of about 150 mg every 12 hours for about 90 days to about six months. In further embodiment, the human subject is administered an initial dose of about 200 mg and is administered a subsequent dose of about 200 mg every 6 hours for about 5 to about 30 days. In yet another embodiment, the human subject is administered an initial dose of about 200 mg and is administered a subsequent dose of about 200 mg every 6 hours for about 30 to about 90 days. In another embodiment, the human subject is administered an initial dose of about 200 mg is administered a subsequent dose of about 200 mg every 6 hours for about 90 days to about six months. In an embodiment of the invention, the human subject is administered an initial dose of about 200 mg and is administered a subsequent dose of about 200 mg every 8 hours for about 5 to about 30 days. In further embodiment, the human subject is administered an initial dose of about 200 mg and is administered a subsequent dose of about 200 mg every 8 hours for about 30 to about 90 days. In yet another embodiment, the human subject is administered an initial dose of about 200 mg and is administered a subsequent dose of about 200 mg every 8 hours for about 90 days to about six months. In another embodiment, the human subject is administered an initial dose of about 200 mg and is administered a subsequent dose of about 200 mg every 12 hours for about 5 to about 30 days. In an embodiment of the invention, the human subject is administered an initial dose of about 200 mg and is administered a subsequent dose of about 200 mg every 12 hours for about 30 to about 90 days. In one embodiment, the human subject is administered an initial dose of about 200 mg and is administered a subsequent dose of about 200 mg every 12 hours for about 90 days to about six months. In another embodiment, the human subject is administered a single or a divided dose of about 25 to about 400 mg of the compound or the pharmaceutical composition, for about between about 5 days to about one year. In yet another embodiment, the human subject is administered a divided dose of about 25 to about 400 mg of the compound, or the pharmaceutical composition, for about between about 5 days to about one year.

Example embodiments of initial and subsequent doses in an adult are shown in Table 1. In certain such embodiments, subsequent doses can be administered from about every 8 hours to about every 96 hours.

TABLE 1

Example Dosing Regimen for an Adult

| Embodiment | Initial dose (mg) | Subsequent dose (mg) |
|---|---|---|
| 1 | 100 | 100 |
| 2 | 150 | 100 |
| 3 | 200 | 100 |
| 4 | 250 | 100 |
| 5 | 300 | 100 |
| 6 | 350 | 100 |
| 7 | 400 | 100 |
| 8 | 450 | 100 |
| 9 | 500 | 100 |
| 10 | 550 | 100 |
| 11 | 600 | 100 |
| 12 | 100 | 150 |
| 13 | 150 | 150 |
| 14 | 200 | 150 |
| 15 | 250 | 150 |
| 16 | 300 | 150 |
| 17 | 350 | 150 |
| 18 | 400 | 150 |
| 19 | 450 | 150 |
| 20 | 500 | 150 |
| 21 | 550 | 150 |
| 22 | 600 | 150 |
| 23 | 600 | 175 |
| 24 | 100 | 200 |
| 25 | 150 | 200 |
| 26 | 200 | 200 |
| 27 | 250 | 200 |
| 28 | 300 | 200 |
| 29 | 350 | 200 |
| 30 | 400 | 200 |
| 31 | 450 | 200 |
| 32 | 500 | 200 |
| 33 | 550 | 200 |
| 34 | 600 | 200 |
| 35 | 100 | 250 |
| 36 | 150 | 250 |
| 37 | 200 | 250 |

TABLE 1-continued

Example Dosing Regimen for an Adult

| Embodiment | Initial dose (mg) | Subsequent dose (mg) |
|---|---|---|
| 38 | 250 | 250 |
| 39 | 300 | 250 |
| 40 | 350 | 250 |
| 41 | 400 | 250 |
| 42 | 450 | 250 |
| 43 | 500 | 250 |
| 44 | 500 | 250 |
| 45 | 550 | 250 |
| 46 | 600 | 250 |
| 47 | 100 | 300 |
| 48 | 150 | 300 |
| 49 | 200 | 300 |
| 50 | 250 | 300 |
| 51 | 300 | 300 |
| 52 | 350 | 300 |
| 53 | 400 | 300 |
| 54 | 450 | 300 |
| 55 | 450 | 300 |
| 56 | 500 | 300 |
| 57 | 500 | 300 |
| 58 | 550 | 300 |
| 59 | 600 | 300 |
| 60 | 40 | 25 |

Example embodiments of initial and subsequent doses combinations in a child are shown in Table 2. In certain such embodiments, subsequent doses can be administered from about ever 8 hours to about ever 96 hours.

TABLE 2

Example Dosing Regimen for a Child

| Embodiment | Initial dose (mg) | Subsequent dose (mg) |
|---|---|---|
| 1 | 15 | 15 |
| 2 | 15 | 25 |
| 3 | 25 | 25 |
| 4 | 50 | 25 |
| 5 | 75 | 25 |
| 6 | 100 | 25 |
| 7 | 150 | 25 |
| 8 | 200 | 25 |
| 9 | 250 | 25 |
| 10 | 300 | 25 |
| 11 | 25 | 50 |
| 12 | 50 | 50 |
| 13 | 75 | 50 |
| 14 | 100 | 50 |
| 15 | 150 | 50 |
| 16 | 200 | 50 |
| 17 | 250 | 50 |
| 18 | 300 | 50 |
| 19 | 25 | 75 |
| 20 | 50 | 75 |
| 21 | 75 | 75 |
| 22 | 100 | 75 |
| 23 | 150 | 75 |
| 24 | 200 | 75 |
| 25 | 250 | 75 |
| 26 | 20 | 20 |
| 27 | 20 | 40 |
| 28 | 25 | 100 |
| 29 | 50 | 100 |
| 30 | 75 | 100 |
| 31 | 100 | 100 |
| 32 | 150 | 100 |
| 33 | 200 | 100 |
| 34 | 250 | 100 |
| 35 | 300 | 100 |
| 36 | 25 | 150 |
| 37 | 50 | 150 |

TABLE 2-continued

| Example Dosing Regimen for a Child | | |
|---|---|---|
| Embodiment | Initial dose (mg) | Subsequent dose (mg) |
| 38 | 75 | 150 |
| 39 | 100 | 150 |
| 40 | 150 | 150 |
| 41 | 200 | 150 |
| 42 | 250 | 150 |
| 43 | 300 | 150 |
| 44 | 25 | 200 |
| 45 | 50 | 200 |
| 46 | 75 | 200 |
| 47 | 100 | 200 |
| 48 | 150 | 200 |
| 49 | 200 | 200 |
| 50 | 250 | 200 |

The compounds or pharmaceutical compositions of the present invention can be administered intravenously, orally, rectally or sublingually. In one embodiment, the route of administration is intravenous. In another embodiment, the route of administration is oral. In another embodiment, the route of administration is rectal. In yet another embodiment, the route of administration is sublingual.

The compounds or pharmaceutical compositions of the present invention can be administered as a single or as a divided dose. In some embodiments, the at least one initial dose can be single, divided, or a combination thereof. In some embodiments, the subsequent doses can be single, divided, or a combination thereof. For the subsequent doses in one embodiment, the human subject is administered a divided dose of from about 25 to about 400 mg for between about 5 to about 30 days. In another embodiment, the human subject is administered the subsequent doses as a single dose of from about 25 to about 400 mg for between about 5 to about 40 days. In yet another embodiment, the human subject is administered the subsequent doses as a single dose of from about 25 to about 400 for between about 5 day to about 60 days. In a further embodiment, the human subject is administered the subsequent doses as a single dose of from about 25 to about 400 mg for between about 5 days to about 60 days. In other versions, the subsequent doses are administered no longer than about 10 days; in yet other versions no longer than about 20 days; in further versions no longer than about 50 days; other versions no longer than about 100 days; and in other versions no longer than about one year.

It is known that a steady state minimum castanospermine concentration of 400 nanograms/ml is associated with a 50 mg/kg BID dose in mice and that the antiviral effect of celgosivir in vivo seems to be correlated with the minimum steady state concentration of castanospermine (Watanabe et al). Literature also shows that the pharmacokinetics of celgosivir is linear with dose over the tolerated dose range (Sorbera et al). International Publication No. WO 2014/143907 discloses pharmacokinetic parameters for castanospermine for the CELADEN study. Pharmacokinetic simulations using those pharmacokinetic parameters suggest that a 4× daily dose of 150 mg should produce a steady state minimum concentration of 1469 nanograms/ml, that a 3× daily dose of 200 mg results in an 799 nanograms/ml steady state minimum concentration of castanospermine, and that 300 mg twice daily results in a steady state minimum concentrations of castanospermine of 532 ng/ml. Extrapolating linearly, therefore, the minimum protective dose (achieving 400 nanograms/ml steady state minimum) is approximately 40 mg every 6 h, 75 mg every 8 h and 225 mg every 12 h. Further, WO 2014/143907 discloses that the CELADEN study regimen produce a steady state maximum castanospermine concentration of 5100 nanograms/ml. The adverse event profile in that study showed a higher incidence of GI effects, but not increased severity at that dose. That study also showed that in theory the maximum daily dose can be as high as 600 mg as a total dose, or 400 mg as a single dose, confirming literature to this effect. The FDA has published generic scaling factors to adjust mg/kg dosing in animals to mg/kg dosing in humans. Generically for mice, that scaling factor is 12. Therefore, 50 mg/kg BID is equivalent to a dose of 4.2 mg/kg BID in humans, which for a 60 kg human is equivalent to 250 mg. The same dose administered three or four times daily is equivalent to 167 mg and 125 mg and 2.8 and 2.1 mg/kg respectively. In a 60 kg human, the maximum single dose is 6.7 mg/kg, and the maximum daily dose is 10 mg/kg.

The invention also relates to methods of treating or preventing a disease resulting from RSV infection by achieving a steady state Cmin serum or plasma concentration of between about 0.05 and about 2.0 microgram/mL of castanospermine in an adult or child subject. In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.3 microgram/mL of castanospermine. In another embodiment, the steady state Cmin serum or plasma concentration achieved in an adult or child subject is between about 0.3 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin serum or plasma concentration achieved in an adult or child subject is between about 1.25 and about 1.75 microgram/mL of castanospermine.

In one embodiment, the minimum steady state concentration of castanospermine achieved exceeds 0.4 microgram/mL during administration of the initial dose(s) and/or subsequent doses to the human subject. In further embodiments, the minimum steady state concentration of castanospermine achieved exceeds 0.5 microgram/mL during administration of the initial dose(s) and/or subsequent doses to the human subject. In yet other embodiments, the minimum steady state concentration of castanospermine achieved exceeds 0.6 microgram/mL during administration of the initial dose(s) and/or subsequent doses to the human subject. In another embodiment, the minimum steady state concentration of castanospermine achieved exceeds 0.7 microgram/mL during administration of the initial dose(s) and/or subsequent doses to the human subject. In still other embodiments, the minimum steady state concentration of castanospermine achieved exceeds 0.8 microgram/mL during administration of the initial dose(s) and/or subsequent doses to the human subject. In other embodiments, the minimum steady state concentration of castanospermine achieved exceeds 0.9 microgram/mL during administration of the initial dose(s) and/or subsequent doses to the human subject. In yet another embodiment, the minimum steady state concentration of castanospermine achieved exceeds 1.0 microgram/mL during administration of the initial dose(s) and/or subsequent doses to the human subject. In some embodiments, the minimum steady state concentration of castanospermine achieved exceeds 1.1 microgram/mL during administration of the initial dose(s) and/or subsequent doses to the human subject. In another embodiment, the minimum steady state concentration of castanospermine achieved exceeds 1.2 microgram/mL during administration of the initial dose(s) and/or subsequent doses to the human subject. In yet another embodiment, the minimum steady state concentration of castanospermine achieved exceeds 1.3 microgram/mL during administration of the initial dose(s) and/or subsequent doses to the human subject. In still other embodiments, the minimum steady state concentration of castanospermine achieved exceeds 1.4 microgram/mL during administration of the initial dose(s) and/or subsequent doses to the human subject. In yet other embodiments, the minimum steady state concentration of castanospermine achieved does not exceed 2.0 microgram/mL during administration of the initial dose (s) and/or subsequent doses to the human subject.

In one embodiment, the average steady state Cmin serum or plasma concentration achieved in the plurality of human subjects is between about 0.08 and about 0.5 microgram/mL of castanospermine. In another embodiment, the average steady state Cmin serum or plasma concentration achieved in the plurality of human subjects is between about 0.05 and about 0.08 microgram/mL of castanospermine. In yet another embodiment, the average steady state Cmin serum or plasma concentration achieved in the plurality of human subjects is between about 0.08 and about 0.11 microgram/mL of castanospermine. In a further embodiment, the average steady state Cmin serum or plasma concentration achieved in the plurality of human subjects is between about 0.11 and about 0.4 microgram/mL of castanospermine. In another embodiment, the average steady state Cmin serum or plasma concentration achieved in the plurality of human subjects is between about 0.4 and about 0.75 microgram/mL of castanospermine. In further embodiment, the average steady state Cmin serum or plasma concentration achieved in the plurality of human subjects is between about 0.75 and about 1.0 microgram/mL of castanospermine. In yet another embodiment, the average steady state Cmin serum or plasma concentration achieved in the plurality of human subjects is between about 1.0 and about 2.0 microgram/mL of castanospermine. In another embodiment, the average steady state Cmin serum or plasma concentration achieved in the plurality of human subjects is between about 1.0 and about 1.5 microgram/mL of castanospermine. In further embodiment, the average steady state Cmin serum or plasma concentration achieved in the plurality of human subjects is between about 1.5 and about 2.0 microgram/mL of castanospermine. In yet another embodiment, the average steady state Cmin serum or plasma concentration achieved in the plurality of human subjects is between about 1.25 and about 1.75 microgram/mL of castanospermine.

In another aspect of the invention, viral load reduction of human subjects receiving the method of treatment is at least 50% greater than in persons not administered the compound or in placebo-administered groups. In one embodiment, the virological log reduction in human subjects receiving the method of treatment is at least 50% greater than in persons not administered the compound or in placebo-administered groups. In another embodiment, the virological log reduction in human subjects receiving the method of treatment is between about 60% to about 70% greater than in persons not administered the compound or in placebo-administered groups. In another embodiment, the virological log reduction in human subjects receiving the method of treatment is between about 70% to about 80% greater than in persons not administered the compound or in placebo-administered groups. In yet another embodiment, the virological log reduction in human subjects receiving the method of treatment is between about 80 to about 90% greater than in persons not administered the compound or in placebo-administered groups.

EXAMPLES

Example 1: Celgosivir is Selectively Active Against RSV In Vitro

The efficacy of celgosivir and castanospermine against RSV and human rhinovirus-14 was assessed in vitro. For RSV studies, embryonic African green monkey kidney cells (MA-104) were grown in minimal essential medium (MEM) supplemented with 0.1% $NaHCO_3$ and 10% fetal bovine serum. When performing antiviral assays, serum was reduced to 2% and 50 mg/ml gentamicin was added to the medium. RSV strain A2 was used for the studies. For rhinovirus studies, the HeLa Ohio cell line was used in place of MA-104 cells.

CPE inhibition assays with visual quantification of antiviral activity and cytotoxicity were performed as described by Sidwell and Huffman (1971) with slight modifications. Sidwell, R. W. and Huffman, J. H. (1971) Use of disposable micro-tissue culture plates for antiviral and interferon induction studies. Appl. Microbiol. 22, 7979-7801. Celgosivir and castanospermine at concentrations of 0.3, 3, 30 and 300 microM and virus at a multiplicity of infection (MOI)=0.001 were added to near confluent cell monolayers 1×10E05 cells/well and incubated at 37° C. until the cells in the control wells showed complete viral CPE as observed by light microscopy (6 days). All compounds were assayed for virus inhibition in quadruplicate and for cytotoxicity in duplicate. For rhinovirus studies, Pirodavir was applied at a concentration of 0.001-1 μg/ml as the positive control compound. For RSV studies, the positive control compound was Ribavirin applied at a concentration of 0.5-500 μg/ml. For each compound, two wells were set aside as uninfected, untreated cell controls per test and four wells per test received virus only and represented controls for virus replication. Changes due to viral cytopathic effect were graded on a scale of 1-4, grade 4 representing a scenario in which the entire (100%) monolayer in a well showed viral cytopathic effect. For all CPE-based assays, the 50% effective concentration (EC50) was calculated by regression analysis using the means of the CPE ratings at each concentration of compound. Morphological changes due to compound cytotoxicity were graded on a scale of 0-5; grade 5 was defined as 100% cytotoxicity. The 50% cytotoxic dose (IC50) was calculated by regression analysis. A selective index (S.I.) was calculated for each compound (SI.=(IC50)/(EC50)).

Neutral red assay of CPE inhibition and cytotoxicity was performed by a modified method as described by Cavenaugh et al. (1990). Cavenaugh, P. R., Jr., Moskwa, P. S., Donish, W. H., Pera, P. J., Richardson, D. and Andrese, A. P. (1990) A semi-automated neutral red based chemosensitivity assay for drug screening. Invest. New Drugs 8, 347-354. Briefly, medium was removed from each well of a plate scored for CPE from the visual CPE inhibition assay, 0.2 ml of neutral red (0.034% in PSS) was added to each of the wells of that plate and the plate incubated for 2 h at 37° C. in the dark. The neutral red solution was removed from the wells and the wells rinsed twice with PBS (pH 7.4). Equal volumes (0.1 ml) of absolute ethanol and Sorenson citrate buffer (0.1 M sodium citrate, 0.1 M HCl, pH 4.2) were mixed together and added to each well. Plates were incubated in the dark for 30 min at room temperature to solubilize the dye. The plates were then gently mixed on a 96-well plate adapted vortexer for 1 min. Absorbances at 540 and 450 nm were read with a microplate reader (Bio-Tek EL 1309; Bio-Tek Instruments). All concentrations were assayed at least in triplicate. Absorbance values were expressed as percentages of untreated controls and EC50 and IC50 values were calculated by regression analysis Results of these studies are set forth in Tables 3 and 4.

TABLE 3

Investigation of celgosivir and castanospermine against human rhinovirus-14

| Assay | Pirodavir $EC_{50}$ | Pirodavir $CC_{50}$ | Pirodavir $SI_{50}$ | Celgosivir HCL $EC_{50}$ | Celgosivir HCL $CC_{50}$ | Celgosivir HCL $SI_{50}$ | Castanospermine $EC_{50}$ | Castanospermine $CC_{50}$ | Castanospermine $SI_{50}$ |
|---|---|---|---|---|---|---|---|---|---|
| Visual examination | 0.032 | >1.0 | >31 | >300 | >300 | N/A | >300 | >300 | N/A |
| Neutral Red | 0.031 | >1.0 | >32 | >300 | >300 | N/A | >300 | >300 | N/A |

TABLE 4

Investigation of celgosivir and castanospermine against RSV

| Assay | Ribavirin $EC_{50}$ | Ribavirin $CC_{50}$ | Ribavirin $SI_{50}$ | Celgosivir HCL $EC_{50}$ | Celgosivir HCL $CC_{50}$ | Celgosivir HCL $SI_{50}$ | Castanospermine $EC_{50}$ | Castanospermine $CC_{50}$ | Castanospermine $SI_{50}$ |
|---|---|---|---|---|---|---|---|---|---|
| Visual examination | 4 | 340 | 85 | 37 | >300 | >8.1 | >300 | >300 | N/A |
| Neutral Red | 2.8 | 62 | 22 | 34 | >300 | >8.8 | >300 | >300 | N/A |

Celgosivir and castanospermine were determined to be safe at all concentrations tested, as the $CC_{50}$ was above the highest concentration tested. Neither celgosivir nor castanospermine were determined to be efficacious against human rhinovirus-14 at the concentrations tested. However, celgosivir was efficacious against RSV infection. Celgosivir produced an $EC_{50}$ of 34-37. Given that the $CC_{50}$ is at least 300, the $SI_{50}$ for celgosivir against RSV is at least 8.1, thus demonstrating the potential usefulness of celgosivir for treatment or prevention of RSV infection in vivo.

Example 2: Celgosivir Reduces RSV-Induced Pulmonary Inflammation in Cotton Rats without Inhibition of Viral Replication

Animals, Dosing Treatment Groups and Infection

Cotton rats [*Sigmodon hispidus,* 2 male & 3 female, 6-8 weeks old] provided with standard rodent chow and water ad lib, were infected intranasally with RSV [strain A/A2, $10^5$ pfu] on Day 0. Animals received celgosivir [25, 50 or 100 mg/kg BID for total daily doses of 50, 100 or 200 mg/kg] daily beginning one day before or after infection and were sacrificed on Day 5-post-infection for histopathology, qPCR, and viral load assessment. Control groups included a [i] positive control Synagis [2.5 mg/kg, i.m, once per day from the first day post-infection], [ii] vehicle control in which vehicle was administered twice per day beginning one day prior to RSV infection, [iii] a vehicle control group that were mock-infected with PBS for which treatment was initiated beginning one day prior to infection, and [iv] an untreated group mock infected with PBS that received no treatment. Animals were weighed on Day −1 and Day 5, and plasma was obtained by retro-orbital bleed on the same days.

The RSV strain for inoculation [A/A2 (RSV A/A2) (ATCC, Manassas, VA)] was propagated in HEp-2 cells after serial plaque-purification to reduce defective-interfering particles. A pool of virus designated containing approximately $3.0\times10^8$ pfu/mL in sucrose stabilizing media was used in the experiment. This stock of virus was stored at −80° C. and was previously characterized in vivo in the cotton rat model and validated for upper and lower respiratory tract replication.

Endpoint Assays Protocol Outline & Stats

Viral Titers: Nose and lung homogenates were centrifuged and diluted in EMEM. Confluent HEp-2 monolayers were infected in duplicate with diluted homogenates in 24-well plates. Following one hour incubation at 37° C. [5% $CO_2$] incubator, wells were overlayed with 0.75% methylcellulose. After 4 days incubation, medium was removed and the cells were fixed with 0.1% crystal violet stain [1 h], then rinsed and air dried. Plaques were counted and virus titer determined as geometric mean plaque-forming units per gram of tissue±standard error for all animals in a group at a given time.

Pulmonary Histopathology: Lungs were removed and inflated with 10% neutral buffered formalin to their normal volume, then fixed [using the same solution]. After fixation, lungs were embedded in paraffin, sectioned, and stained with H&E. Four parameters of pulmonary inflammation were evaluated: peribronchiolitis (inflammatory cell infiltration around the bronchioles), perivasculitis (inflammatory cell infiltration around the small blood vessels), interstitial pneumonia (inflammatory cell infiltration and thickening of alveolar walls), and alveolitis (cells within the alveolar spaces). Slides were blindly scored on a 0-4 severity scale. The scores are subsequently converted to a 0-100% normalized scale.

Statistics: Group means for each parameter were evaluated by one-way ANOVA, then individual group means were compared [t-test, with multiple comparison correction] to the RSV-infected, vehicle-treated control group. $P<0.05$ was considered statistically significant.

Figure 2:
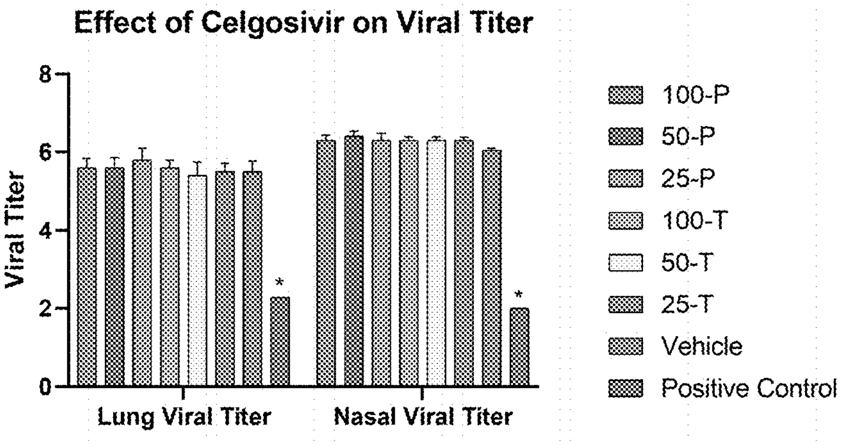
FIG. 2: Effect of celgosivir on viral titer. Groups of five cotton rats were administered 25, 50 or 100 mg/kg celgosivir twice per day beginning one day prior to infection [prophylaxis, P] or one day after infection [treatment, T], drug vehicle twice per day beginning one day prior to infection [vehicle], or synagis [2.5 mg/kg i.m.] once per day beginning the day after infection [positive control]. On the fifth day post infection, animals were sacrificed and nasal and lung viral titers were determined. The positive control treatment decrease viral titer but celgosivir did not. Statistical significance from the vehicle control is indicated by an asterix [P<0.05].

Outcomes: Results of the studies are shown in FIGS. 1 and 2. Celgosivir reduced inflammation at all doses on three of four histopathology parameters, with a dose-effect evident when the drug was administered beginning one day prior to infection on two of the histopathology domains. The positive control antiviral exhibit statistically significant reductions across all four histopathology domains. Celgosivir exhibited no effect on viral titer in either the nose or the lung. Celgosivir exhibited no discernable effect on nasal or lung viral titer.

The data demonstrate that celgosivir reduces the extent of RSV-induced pulmonary histopathological changes in a manner independent of an inhibitory effect on viral replication in the nose or lung.

Example 3: Delayed Parenteral Administration of Celgosivir or Castanospermine is Expected to be Protective Against RSV-Induced Histopathological Changes Utilizing the methodology outlined in Example 2, it is evident from examination of the data in FIG. 1, that timing of celgosivir administration has minimal impact on the degree of protection against inflammation conferred by the drug. This is in contrast to other viral diseases against which celgosivir is active via an antiviral mechanisms, but for which the timing of administration has a profound impact upon the degree of benefit provided.

Castanospermine administered parenterally confers antiviral activity, and celgosivir administered parenterally is rapidly converted to castanospermine, meaning that the actual therapeutic scaffold in vivo is castanospermine. Therefore, it is predicted that the administration of celgosivir or castanospermine parenterally, after viral exposure and initiation of symptoms of disease, in animals or humans, will protect the treated subject from RSV-induced pulmonary inflammation and reduced lung function.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating disease resulting from a respiratory syncytial virus (RSV) infection in a human subject, comprising:

(a) determining that the human subject is infected with RSV;

(b) administering to the human subject at least one initial dose of about 15 to about 600 mg of a compound of Formula (II) or a pharmaceutically acceptable salt thereof, or a pharmaceutical composition comprising about 15 to about 600 mg of a compound of Formula (II) or a pharmaceutically acceptable salt thereof; and (c) administering to the human subject a plurality of subsequent doses of about 15 to about 400 mg of a compound of Formula (II) or a pharmaceutically acceptable salt thereof, or a pharmaceutical composition comprising about 15 to about 400 mg of a compound of Formula (II) or a pharmaceutically acceptable salt thereof, wherein not more than 600 mg of a compound of Formula (II) is administered per day, wherein said subsequent doses are administered once, twice, three, or four times per day, and wherein Formula (II) has the following structure, (II)

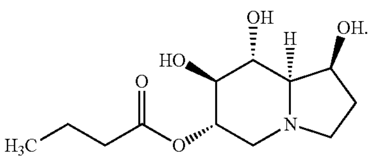

2. The method of claim 1, wherein the compound of Formula (I) is converted to castanospermine after administration to said human subject, and wherein a steady state Cmin serum or plasma concentration of between about 0.4 and about 2.0 microgram/mL of castanospermine is attained in the human subject after administrations of initial and subsequent doses.

3. The method of claim 1, wherein the compound, or the pharmaceutical composition, is administered orally or sublingually.

4. The method of claim 1, wherein the human subject is administered an initial dose of about 150 mg and is administered a subsequent dose of about 100 mg every 6 hours, 8 hours, or 12 hours for between about 5 days to about 30 days.

5. The method of claim 1, wherein the human subject is administered an initial dose of about 150 mg and is administered a subsequent dose of about 150 mg every 6 hours, every 8 hours, or every 12 hours for between about 5 days to about 30 days.

6. The method of claim 1, wherein the human subject is administered an initial dose of about 200 mg and is administered a subsequent dose of about 100 mg every 6 hours, 8 hours, or 12 hours for between about 5 days to about 30 days.

7. A method of claim 1, wherein the human subject is administered an initial dose of about 200 mg and is administered a subsequent dose of about 150 every 6 hours, 8 hours, or 12 hours for between about 5 days to about 30 days.

8. The method of claim 1, wherein the human subject is administered an initial dose of about 200 mg and is administered a subsequent dose of about 200 mg every 6 hours, 8 hours, or 12 hours for between about 5 days to about 30 days.

9. The method of claim 1, wherein the human subject is administered celgosivir or castanospermine to reduce pulmonary inflammation or improve lung function.

10. The method of claim 1, wherein the human subject is administered celgosivir or castanospermine intravenously or intramuscularly, where in the human subject receives a total daily dose of at least 4 mg/kg/day, but no more than 12 mg/kg/day, administered as a split dose at least twice, but up to four times per day.

11. A method of preventing a disease resulting from a respiratory syncytial virus (RSV) infection in a human subject, comprising:

(a) administering to the human subject at least one initial dose of about 15 to about 600 mg of a compound of Formula (I) or a pharmaceutically acceptable salt thereof, or a pharmaceutical composition comprising about 15 to about 600 mg of a compound of Formula (I) or a pharmaceutically acceptable salt thereof; and (b) administering to the human subject a plurality of subsequent doses of about 15 to about 400 mg of a compound of Formula (I) or a pharmaceutically acceptable salt thereof, or a pharmaceutical composition comprising about 15 to about 400 mg of a compound of Formula (I) or a pharmaceutically acceptable salt thereof, wherein not more than 600 mg of a compound of Formula (I) is administered per day, wherein the human subject is asymptomatic at the time of administration of the at least one initial dose, wherein said subsequent doses are administered once, twice, three, or four times per day, and wherein Formula (I) has the following structure, (I)

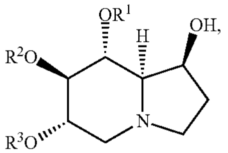

wherein $R^1$, $R^2$, and $R^3$ are independently H, $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

12. The method of claim 11, wherein the compound of Formula (I), is a compound of Formula (II):

(II)

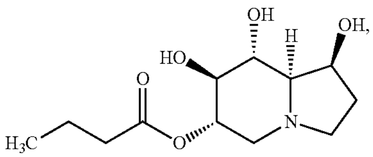

and wherein the human subject is a child less than one year of age.

13. The method of claim 11, wherein the compound of Formula (I) is converted to castanospermine after administration to said human subject, and wherein a steady state Cmin serum or plasma concentration of between about 0.4 and about 2.0 microgram/mL of castanospermine is attained in the human subject after administrations of initial and subsequent doses.

14. The method of claim 11, wherein the compound, or the pharmaceutical composition, is administered orally or sublingually.

15. The method of claim 11, wherein the human subject is administered an initial dose of about 150 mg and is administered a subsequent dose of about 100 mg every 6 hours, 8 hours, or 12 hours for between about 5 days to about 30 days.

16. The method of claim 11, wherein the human subject is administered an initial dose of about 150 mg and is administered a subsequent dose of about 150 mg every 6 hours, every 8 hours, or every 12 hours for between about 5 days to about 30 days.

17. The method of claim 11, wherein the human subject is administered an initial dose of about 150 mg and is administered a subsequent dose of about 200 mg every 6 hours, 8 hours, or 12 hours for between about 5 days to about 30 days.

18. The method of claim 11, wherein the human subject is administered an initial dose of about 200 mg and is administered a subsequent dose of about 100 mg every 6 hours, 8 hours, or 12 hours for between about 5 days to about 30 days.

19. The method of claim 11, wherein the human subject is administered an initial dose of about 200 mg and is administered a subsequent dose of about 150 every 6 hours, 8 hours, or 12 hours for between about 5 days to about 30 days.

20. The method of claim 11, wherein the human subject is administered an initial dose of about 200 mg and is administered a subsequent dose of about 200 mg every 6 hours, 8 hours, or 12 hours for between about 5 days to about 30 days.

* * * * *